United States Patent [19]

Lohmann et al.

[11] 4,364,808
[45] Dec. 21, 1982

[54] PHOTOCHEMICAL PREPARATION OF SILANES CONTAINING IMIDE GROUPS

[75] Inventors: Dieter Lohmann, Muttenz; Siegfried Wyler, Dornach, both of Switzerland

[73] Assignee: Ciba-Geigy Corporation, Ardsley, N.Y.

[21] Appl. No.: 216,355

[22] Filed: Dec. 15, 1980

Related U.S. Application Data

[62] Division of Ser. No. 67,864, Aug. 20, 1979, Pat. No. 4,271,074.

[30] Foreign Application Priority Data

Aug. 30, 1978 [CH] Switzerland ............... 9154/78

[51] Int. Cl.³ .................................... B01J 19/12
[52] U.S. Cl. .......................................... 204/158 R
[58] Field of Search .............................. 204/158 R

[56] References Cited

U.S. PATENT DOCUMENTS

| | | |
|---|---|---|
| 2,901,913 | 9/1959 | Lovegrove . |
| 3,274,155 | 9/1966 | Saunders et al. . |
| 3,576,031 | 4/1971 | Holub et al. . |
| 3,655,691 | 4/1972 | Page . |
| 3,755,354 | 8/1973 | Holub et al. . |
| 3,901,913 | 8/1975 | Kim . |
| 3,956,353 | 5/1976 | Plueddemann . |
| 3,966,531 | 6/1976 | Bargain . |
| 4,152,346 | 5/1979 | Seiler et al. . |
| 4,271,074 | 6/1981 | Lohmann et al. . |

FOREIGN PATENT DOCUMENTS 2626795 12/1976 Fed. Rep. of Germany .

OTHER PUBLICATIONS

B. W. Lipinski, Defazet, 28, 207 (1974).
F. Hoersch, Kunststoffe, 55, 909 (1965).
R. H. Yocum et al., "Functional Monomers", vol. 2, Dekkar, New York, 1974, p. 234.
N. Boens et al., J. Polymer Sci. (Poly. Chem. Ed.), 13, 201 (1975).

Primary Examiner—Howard S. Williams
Attorney, Agent, or Firm—Luther A. R. Hall

[57] ABSTRACT

The compounds according to the invention have the formula I

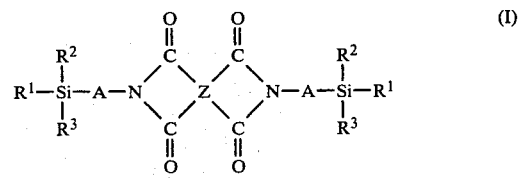

in which $R^1$, $R^2$ and $R^3$ are monovalent organic radicals or chlorine and Z is a tetravalent organic radical and A is a divalent organic grouping. These products are to be used as adhesion promoters, especially between inorganic solids and organic resins. 4 processes of preparation are given.

5 Claims, No Drawings

PHOTOCHEMICAL PREPARATION OF SILANES CONTAINING IMIDE GROUPS

This is a divisional of application Ser. No. 67,864, filed on Aug. 20, 1979, now U.S. Pat. No. 4,271,074, issued on June 2, 1981.

The present invention relates to novel silanes containing imide groups, processes for their preparation and their use as adhesion promoters, for example between inorganic solids and organic resins.

It is known from the literature that diverse silanes, such as vinyltrichlorosilane, vinyl-tris-(2-methoxyethoxy)-silane, γ-aminopropyltriethoxysilane and [N-(2-aminoethyl)-3-aminopropyl]-trimethoxysilane, can be used as adhesion promoters for diverse applications, for example for the preparation of glass fibre-reinforced plastics, especially laminate sheets for electrical applications, and for sealing compositions, lacquers and adhesives [compare, for example, Defazet, 28, 207–211 (1974) and Kunststoffe, 55, 909–912 (1965), U.S. Pat. Nos. 3,901,913 and 3,755,354 and German Offenlegungsschrift No. 2,504,791].

However, the properties of the products obtained with these known adhesion promoters leave something to be desired in some respects. The products are to be regarded as very unfavourable especially in respect of one or more of the following 3 properties: absorption of water, thermo-oxidative stability and dielectric characteristics.

The object of the invention was, therefore, to provide novel adhesion promoters with which the above disadvantages can be overcome.

The invention relates to compounds of the formula I $$\begin{array}{c}
\text{R}^2 \quad \overset{O}{\underset{\parallel}{C}} \quad \overset{O}{\underset{\parallel}{C}} \quad \text{R}^2 \\
\text{R}^1-\text{Si}-\text{A}-\text{N} \diagdown_{C}^{\diagup} Z \diagdown_{C}^{\diagup} \text{N}-\text{A}-\overset{|}{\text{Si}}-\text{R}^1 \\
\overset{|}{\text{R}^3} \quad \underset{\parallel}{C} \quad \underset{\parallel}{C} \quad \overset{|}{\text{R}^3} \\
\quad \quad O \quad O
\end{array} \quad (I)$$

in which the two rings which each contain a N atom and the radical Z are preferably 5-membered or 6-membered rings and in which $R^1$ and $R^2$ independently of one another are methyl, ethyl, phenyl, vinyl, chlorine or a group —OR, $R^3$ is chlorine or —OR, R is alkyl having 1–10 C atoms, cycloalkyl having 5–8 C atoms or phenyl, Z is a tetravalent aliphatic radical, which can be interrupted by hetero-atoms, or a substituted or unsubstituted tetravalent cycloaliphatic radical, which can contain hetero-atoms and/or can be fused with a benzene ring, A is a substituted or unsubstituted, divalent, saturated or unsaturated, aliphatic, cycloaliphatic, aliphatic-aromatic or aromatic radical (it being possible for aliphatic radicals A or aliphatic moieties of aliphatic-aromatic radicals A to be interrupted by hetero-atoms), or a grouping

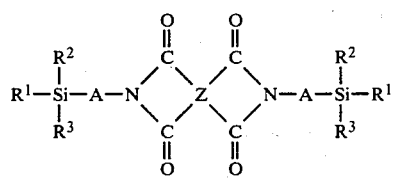

or a grouping

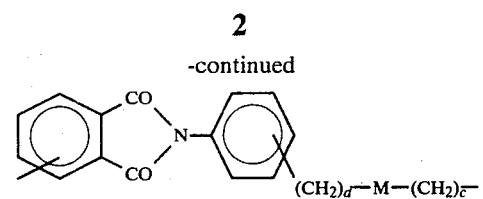

and in the two last-mentioned groupings the bond to the particular N atom is effected via the free valency on the benzene nuclei, $R^{10}$ is hydrogen, methyl or ethyl, $R^{11}$ is hydrogen or alkyl having 1 to 10 C atoms, d is a number from 0 to 6, c is a number from 1 to 6 and M is —O—, —NH— or —N($R^{11}$)—.

Tetravalent aliphatic radicals Z can be straight-chain or branched and/or interrupted by one or more hetero-atoms, in particular N atoms. The radicals are in particular alkanetetrayl groups having 2–8 C atoms, which can be interrupted by N atoms, such as the groups

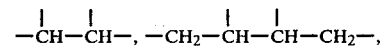

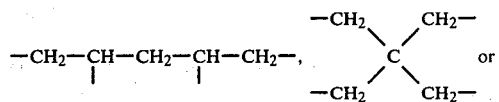

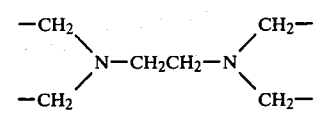

A preferred form of the compounds according to the invention comprises those substances in which, in formula I, Z is one of the groupings

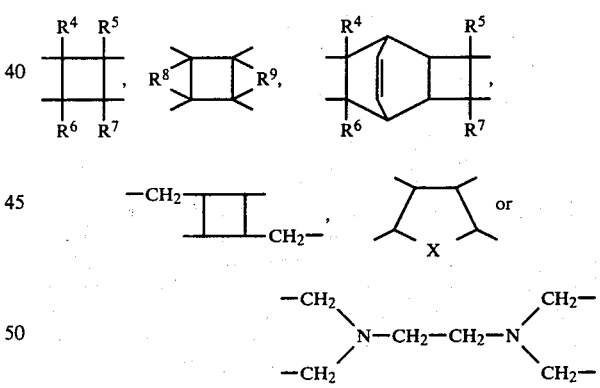

and A is one of the divalent radicals —(CH$_2$)$_a$—, —C($R^{10}$)$_2$—CH=C($R^{11}$)—, —C($R^{10}$)$_2$—CH($R^{11}$)—, —(CH$_2$)$_b$—G—(CH$_2$)$_c$—, phenylene—(CH$_2$)$_d$—G—(CH$_2$)$_c$—, phenylene—(CH$_2$)$_d$—,

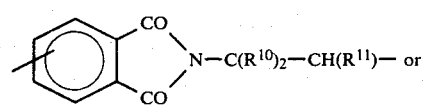

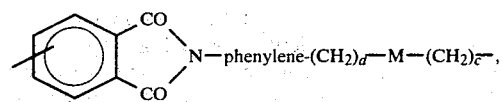

and in these divalent radicals A the bond to the Si atom is in each case effected via the bond on the right-hand side and, in the above groupings and radicals, d, c, M, $R^{10}$ and $R^{11}$ are as defined above, and $R^4$, $R^5$, $R^6$ and $R^7$ independently of one another are hydrogen, methyl, phenyl, —CN or halogen, $R^8$ and $R^9$ independently of one another are alkylene having 3 or 3 C atoms, which can be branched and can be interrupted by a hetero-atom, especially —O—, or are one of the radicals

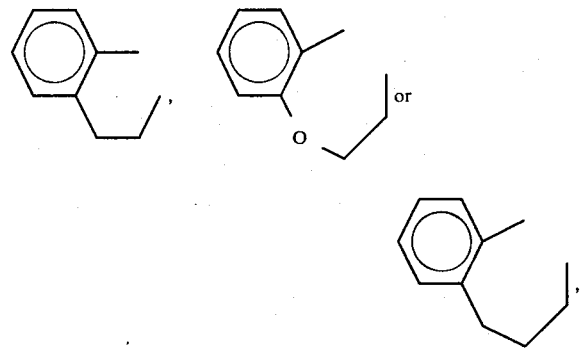

a is 1 to 10, b is 1 to 6, G is —CH($R^{11}$)—, —NH—, —N($R^{11}$)—, —O— or phenylene and X is —CH$_2$— or —O—.

Particularly preferred compounds are those in which, in formula I, Z is the grouping

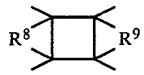

in which $R^8$ and $R^9$ are each

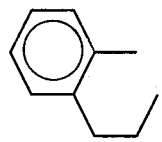

and compounds in which, in formula I, $R^1$ is methyl, $R^2$ and $R^3$ independently of one another are alkoxy having 1-3 C atoms, cyclohexyloxy or phenoxy, $R^4$, $R^5$, $R^6$ and $R^7$ independently of one another are hydrogen or methyl, $R^8$ and $R^9$ are each tetramethylene, $R^{10}$ is hydrogen or methyl, $R^{11}$ is hydrogen, a is a number from 1 to 6, b and c independently of one another are 2 or 3, d is a number from 0 to 3, G is —O— or —NH— and M is —O—.

Very particularly preferred compounds according to the invention have the formula II $$\text{(II)}$$

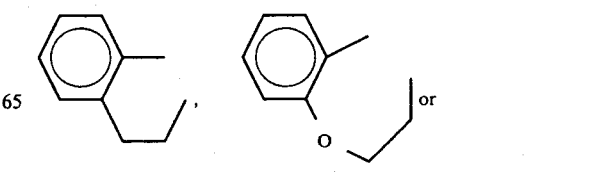

in which a' is 2 or 3 and $R^4$, $R^5$, $R^6$ and $R^7$ are each hydrogen and in particular are each methyl.

Diverse processes can be used for the preparation of the silicon compounds according to the invention. The first process to be listed is a photochemical process (A), which in general results in a composition of matter or reaction mixture which can be employed direct as an adhesion promoter. Reaction mixtures of this type are obtained by irradiating a compound of the formula III

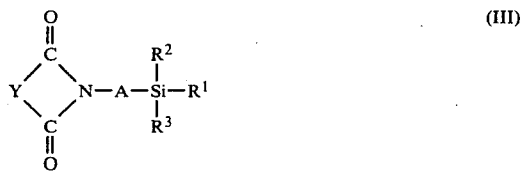

or a mixture of different compounds of the formula III, in which $R^1$ and $R^2$ independently of one another are methyl, ethyl, phenyl, vinyl, chlorine or a group —OR, $R^3$ is chlorine or —OR, R is alkyl having 1-10 C atoms, cycloalkyl having 5-8 C atoms or phenyl, A is a substituted or unsubstituted, divalent, saturated or unsaturated, aliphatic, cycloaliphatic, aliphatic-aromatic or aromatic radical (it being possible for aliphatic radicals A or aliphatic moieties of aliphatic-aromatic radicals A to be interrupted by hetero-atoms) or a grouping

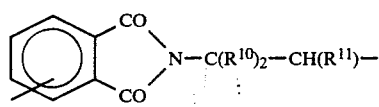

or a grouping

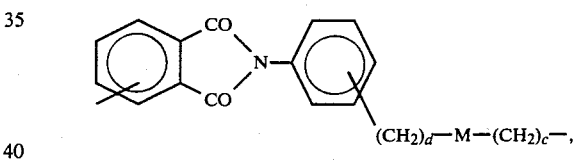

and in the two last-mentioned groupings the bond to the particular N atom is effected via the free valency in the benzene nuclei, $R^{10}$ is hydrogen, methyl or ethyl, $R^{11}$ is hydrogen or alkyl having 1 to 10 C atoms, d is a number from 0 to 6, c is a number from 1 to 6 and M is —O—, —NH— or —N($R^{11}$)—, and in which Y is

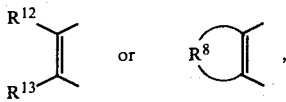

$R^{12}$ and $R^{13}$ independently of one another are hydrogen, methyl, phenyl, —CN or halogen and $R^8$ is alkylene having 3 or 4 C atoms, which can be branched and can be interrupted by a hetero-atom, especially by —O—, or is one of the radicals

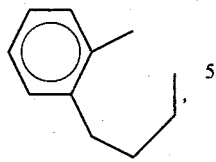

in an organic solvent and if desired in the presence of a sensitiser and/or benzene, at temperatures between 5° C. and 120° C. with UV light.

Organic solvents which can be used for this process are, for example, dioxan or acetone. Suitable sensitisers are, for example, thioxanthones, which can be halogenated, benzophenone and acetophenone.

In general, the reaction mixtures contain in particular dimers according to the invention and oligomers, and can also contain monomers of the formula III. In principle, however, they can by all means also contain yet further by-products.

During the reaction it is in the main a cyclobutane ring, as has already been shown above when defining the tetravalent radical Z in the formula I, which is formed, with dimerisation of the silane of the formula III.

If the photochemical reaction is carried out in the presence of benzene, a Diels-Alder reaction can also proceed alongside the photoaddition reaction and substances are formed which can have, for example, the following structure:

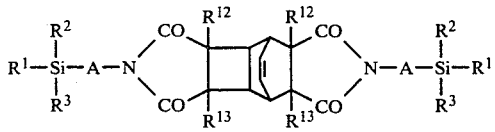

If it is desired to obtain pure dimerised silanes of the formula III, which correspond to the formula I in a correspondingly restricted form, these must be separated off by known processes, for example by precipitation and recrystallisation or by chromatography.

The reaction mixture obtainable by the process described is also particularly effective as an adhesion promoter in the sense of this invention. For use as an adhesion promoter, it is possible, in principle, to employ direct the solution or emulsion which is obtained after carrying out the process of preparation described. However, it is also possible first to separate off the organic solvent and any benzene used in the preparation and to re-dissolve the residual composition of matter in a suitable solvent, for use as an adhesion promoter. These two procedures for use of the resulting products, i.e. the use of the solution or emulsion originally obtained or use of the products which are first isolated and then re-dissolved, can also be applied in the case of the products according to the invention which are prepared by the processes described below.

A further process (B) for the preparation of silanes of the formula I comprises reacting a compound of the formula IV

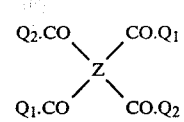

in which Z is as defined under formula I and in which $Q_1$ is —OH, chlorine, alkoxy having 1-6 C atoms or phenoxy and $Q_2$ is alkoxy having 1-6 C atoms or phenoxy, or $Q_1$ and $Q_2$, in pairs, form the grouping —O—, with a compound of the formula V

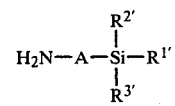

in which A is as defined under formula I and in which $R^{1'}$, $R^{2'}$ and $R^{3'}$ have the meanings defined for $R^1$, $R^2$ and $R^3$ under formula I but cannot be chlorine, in approximately stoichiometric amounts, if desired with a slight excess of the silane of the formula V, and if desired in the presence of an organic solvent, to give the amidocarboxylic acid of the formula VI

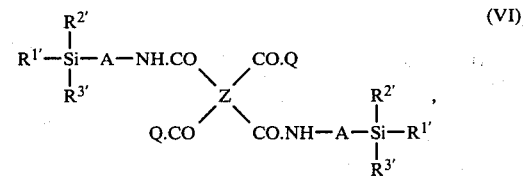

in which Q is —OH, alkoxy having 1-6 C atoms or phenoxy, and cyclising the amidocarboxylic acid of the formula VI, which is thus obtained, in a known manner, if desired in the presence of an inert organic solvent, to a compound of the formula I and, if desired, in this compound replacing one or more —OR groups by chlorine in a known manner. The amidocarboxylic acids of the formula VI can also be applied direct to the substrate and cyclised on the substrate.

Virtually all of the compounds of the formula I can be prepared by this process (B). Solvents which can be used are, for example, N,N-dimethylformamide, N,N-dimethylacetamide, benzene, toluene, xylene, dioxan or n-hexane.

A further process (C) for the preparation of the products according to the invention is limited to the preparation of those compounds of the formula I in which A is one of the divalent radicals

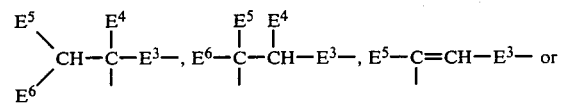

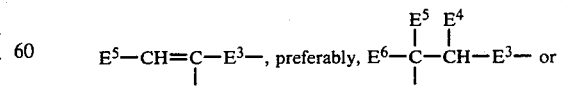

which in each case are bonded via $E^3$ to the N atoms and in which $E^3$ is a direct bond, alkylene having 1 to 8

C atoms, cyclohexylene, phenylene or —CH₂—phenylene, which is bonded via the —CH₂ group to the N atoms, and E⁴ and E⁶ independently of one another are hydrogen, methyl or ethyl and E⁵ is hydrogen or alkyl having 1 to 9 C atoms. This process comprises reacting a compound of the formula VII

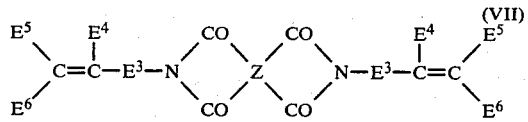

or a compound of the formula VIII

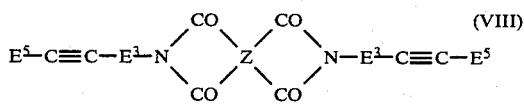

in the presence of a noble metal or of a noble metal compound or in the presence of an organic peroxide or, alternatively, under UV radiation and if desired in the presence of an inert organic solvent, with a silane of the formula

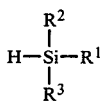

in which R¹, R² and R³ are as defined under formula I, in a molar ratio of about 1:2.

Solvents which can be employed for this process are, for example, toluene, benzene, xylene or dioxan.

Suitable noble metal catalysts are the known catalysts, for example platinum black or palladium black, colloidal platinum, or palladium or rhodium on a support material, such as active charcoal or kieselguhr. Suitable noble metal compounds are inorganic salts, for example halides, and complexes, for example those with phosphines. H₂PtCl₆ is preferably used.

Organic peroxides suitable as catalysts are, for example, dibenzoyl peroxide, dilauroyl peroxide, methyl ethyl ketone peroxide, cumene hydroperoxide and tert.-butyl hydroperoxide.

Finally, a further process (D), with which it is possible to prepare products according to the invention, must also be listed. This process of preparation (D) comprises subjecting a di-(alkali metal) compound, preferably the di-Na or di-K compound

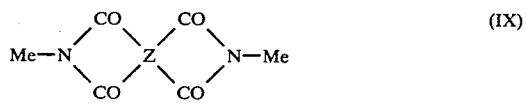

in which Me is the alkali metal, to a condensation reaction with a silane of the formula X

in which L is halogen, preferably chlorine or bromine, and in which R¹', R²', and R³', have the meanings defined for R¹, R² and R³ in formula I but cannot be chlorine, in approximately stoichiometric amounts, if desired with a slight excess of the silane of the formula X, and if desired in the presence of an inert organic solvent, preferably at temperatures between 25° C. and 150° C., and, if desired, replacing one or more —OR groups located on the silicon atom by chlorine in a known manner.

Solvents which can be employed for this process are, for example, N,N-dimethylformamide, N,N-dimethylacetamide, methanol or ethanol.

If products of the formula I in which all or some of R¹, R² and R³ are chlorine are obtained by one of the process (A) to (D), chlorine can also be replaced by a radical —OR by known methods in a secondary reaction.

In detail, the following is to be stated with regard to the starting materials for the processes of preparation (A–D) described. The silanes for process (A), which contain a substituted or unsubstituted maleimide group and have the formula III and which themselves can also be employed as adhesion promoters, are known in some cases and can be prepared, for example, by the processes described in U.S. Pat. Nos. 3,576,031 and 3,755,354. Thus, these silanes can be prepared, for example, by reacting an amino-organoalkoxysilane of the formula

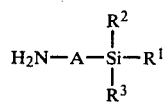

with a substituted or unsubstituted maleic anhydride to give the corresponding amidoacid-silane and then cyclising the latter to the maleimide-silane.

The tetracarboxylic acid derivatives of the formula IV and the aminosilanes of the formula V, which are to be used for process of preparation (B), are likewise known or can be prepared by known methods.

The alkali metal compounds of the formula IX and the silanes of the formula X, which are required for the condensation process (D), can be prepared by known methods. Thus, for example, alkali metal compounds which contain only one imide group and are analogous to the compounds of the formula IX are described in German Offenlegungsschrift No. 2,626,795. The silanes of the formula X are known or can be prepared by known methods.

The bis-imides of the formula VII and VIII, which are used as starting materials for the addition process (C), are novel. If E³ in the formulae VII and VIII is an alkylene radical having 1–8 C atoms, cyclohexylene, phenylene or —CH₂-phenylene with the —CH₂ group bonded to the N atom, these starting materials can be prepared, for example, by reacting a compound of the formula IV

with an amine of the formula XI

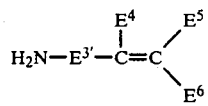

(XI)

or of the formula XII $$H_2N\text{-}E^{3'}\text{—}C\equiv C\text{—}E^5 \tag{XII}$$

and cyclising the amidocarboxylic acids of the formula XIII

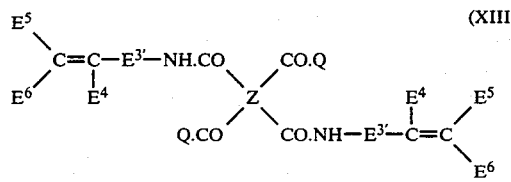

(XIII)

or of the formula XIV

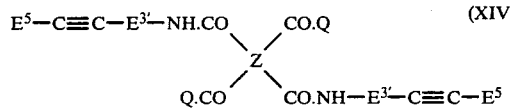

(XIV)

which are formed in the particular case; formula IV corresponds to the formula IV given in the description of process of preparation (B) and $E^{3'}$ is alkylene having 1-8 C atoms, cyclohexylene, phenylene or —CH$_2$-phenylene with the —CH$_2$ group bonded to the N atom.

Preferred compounds of the formula IV are the dianhydrides.

The reactants are employed in approximately stoichiometric amounts, but a slight excess of the amines of the formula XI or XII can also be employed.

The reaction of the compound of the formula IV with the amines of the formulae XI or XII and also the subsequent cyclisation of the amidocarboxylic acids are advantageously carried out in an inert organic solvent, such as N,N-dimethylformamide, N,N-dimethylacetamide, benzene, toluene, xylene, n-hexane or chloroform. However, the reaction can also be carried out without the additional use of an organic solvent.

The reaction temperatures for the reaction of the compound of the formula IV with the amines are in general between about 20° and 180° C. The cyclisation can be effected by azeotropic removal of the water of reaction formed, by the addition of conventional dehydrating agents, such as acetic anhydride or propionic anhydride, if desired as a mixture with tertiary amines, such as triethylamine or pyridine, or sodium acetate, or, alternatively, in the presence of water-binding agents, such as molecular sieves.

If $E^3$ in the formulae VII and VIII is a direct bond, alkylene having 1 to 8 C atoms, cyclohexylene or —CH$_2$-phenylene with the —CH$_2$ group bonded to the N atom, these starting materials can also be prepared by subjecting a compound of the formula IX

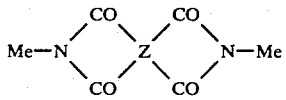

(IX)

to a condensation reaction with a compound of the formula XV

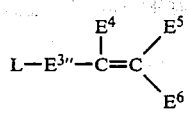

(XV)

or of the formula XVI $$L\text{-}E^{3'''}\text{—}C\equiv C\text{—}E^5 \tag{XVI}$$

in which L is halogen, preferably chlorine or bromine, and $E^{3'''}$ is a direct bond, alkylene having 1 to 8 C atoms, cyclohexylene or —CH$_2$-phenylene with the —CH$_2$ group bonded to G-, and $E^{42}$, $E^5$ and $E^6$ are as defined for formulae VII and VIII, in approximately stoichiometric amounts, if desired with a slight excess of the compounds of the formulae XV or XVI, in the melt or in the presence of an inert organic solvent.

Finally, the starting materials of the formulae VII or VIII can also be prepared by a photochemical reaction in those cases in which Z in these formulae is in each case one of the tetravalent radicals

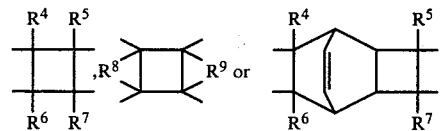

in which $R^4$ to $R^9$ are as defined above. When carrying out this process, a compound of the formula XVII

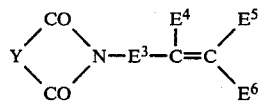

(XVII)

or of the formula XVIII

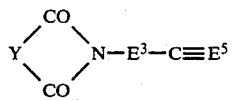

(XVIII)

in which Y is as defined under formula III, in an organic solvent and if desired in the presence of a sensitiser and/or benzene, is irradiated with UV light. In other respects, this dimerisation corresponds to process (A) for the preparation of the silanes according to the invention, so that in this case also the same and analogous reaction conditions are to be employed.

The invention also relates to compounds of the formula XIX

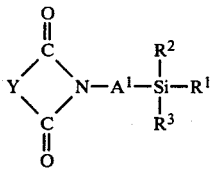

XIX in which $R^1$ and $R^2$ independently of one another are methyl, ethyl, phenyl, vinyl, chlorine or a group —OR, $R^3$ is chlorine or —OR, R is alkyl having 1–10 C atoms, cycloalkyl having 5–8 C atoms or phenyl, $A^1$ is one of the divalent radicals —$(CH_2)_a$—, —$C(R^{10})_2$—CH=$C(R^{11})$—, —$C(R^{10})_2$—$CH(R^{11})$—, —$(CH_2)_b$—G—$(CH_2)_c$—, phenylene—$(CH_2)_d$—G—$(CH_2)_c$, phenylene-$(CH_2)_d$—,

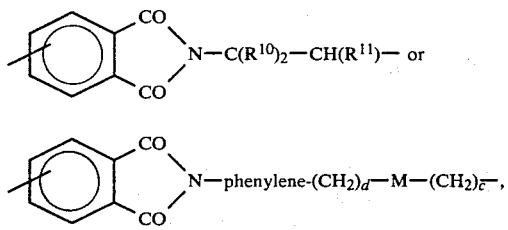

and in these divalent radicals A the bond to the Si atom is in each case effected via the bond on the right-hand side, $R^{10}$ is hydrogen, methyl or ethyl, $R^{11}$ is hydrogen or alkyl having 1 to 10 C atoms, a is a number from 1 to 10, b and c independently of one another are a number from 1 to 6, d is a number from 0 to 6, G is —$CH(R^{11})$—, —NH—, —$N(R^{11})$—, —O— or phenylene and M is —O—, —NH— or —$N(R^{11})$—, and in which Y is

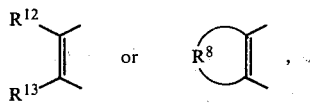

$R^{12}$ is hydrogen, methyl, phenyl, —CN or halogen, $R^{13}$ is methyl, phenyl, —CN or halogen and $R^8$ is alkylene having 3 or 4 C atoms, which can be branched and can be interrupted by a hetero-atom, especially by —O—, or is one of the radicals

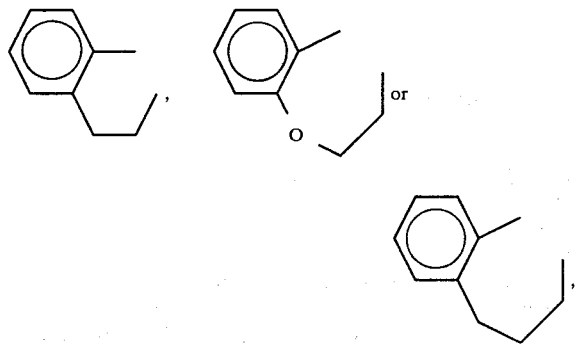

with the proviso that $A^1$ cannot be

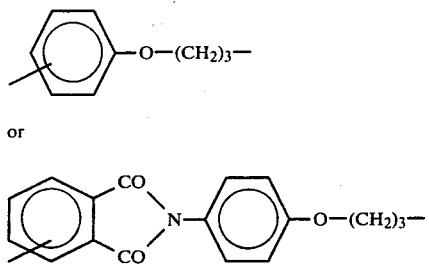

if $R^{12}$ and $R^{13}$ are each methyl.

The silanes of the formula XIX are likewise particularly suitable as adhesion promoters and are superior to the known adhesion promoters mentioned initially. The invention therefore also relates to the use of the silanes of the formula XIX as adhesion promoters and to the processes for the preparation of these compounds.

The silanes of the formula XIX can also be used as starting materials for the photochemical process (A), for the preparation of compounds of the formula I or of reaction mixtures containing compounds of the formula I, which has been claimed.

The novel silanes of the formula XIX can be prepared by processes B', C' and D', which are analogous to processes (B), (C) and (D) for the preparation of the compounds of the formula I according to the invention. In this case, however, in place of difunctional starting compounds of the formulae IV, VII, VIII and IX, corresponding monofunctional compounds which contain the divalent radical Y in place of the tetravalent radical Z are in each case used as the starting materials.

The silanes of the formula I and XIX, according to the invention, and also the products obtained by photo-reaction of compounds of the formula III are valuable adhesion promoters, especially between inorganic solids and organic resins, and are suitable for a large number of applications in the adhesives industry and in the lacquer-processing and plastics-processing industry.

Examples of some fields of application are: for improving the adhesion of specific sealing compositions, for example polysulfides, polyurethanes and polyacrylates, on diverse substrates, such as glass, aluminum and ceramics; for coating mineral fillers in order to improve the mechanical properties of the products produced therewith, for example in the case of the sand-filled shells and cores used in the foundry industry, mineral-filled cable mixtures or other mineral-filled plastics, for example filled thermosetting plastics, such as quartz-filled epoxide resins and filled unsaturated polyesters, filled thermoplastics, such as polyamide 6,6 and polyethylene terephthalate, and filled elastomers, such as natural and synthetic rubber; and for adhesives, adhesive compositions and epoxide, polyacrylate, polyurethane and vinyl chloride copolymer lacquers. The said compounds are, however, in particular suitable for the preparation of reinforced plastics, especially glass fibre-reinforced plastics, especially composite materials, such as laminates for electrical applications, in order to improve the adhesion between the substrate or the matrix and the plastic applied thereto. The substrate can be in any form per se, for example in the form of fibres, fabrics or nonwovens, and preferably consists of glass or, alternatively, of mineral substances, such as quartz, rock wool, asbestos, mica or metallic fibres and foils. Suitable plastics for the preparation of such laminates are, for example, acrylates and polyester, epoxide, silicone, melamine, phenol and furan resins; and also polyamides and polyamide-acids or polyimides, but especially polymers which are crosslinkable via C=C double bonds, such as unsaturated polyesters and homo- and copolymers which contain maleimidyl or nadicimidyl groups, their precursors or mixtures with other polymers.

Compared with silicon-containing adhesion promoters previously known, the adhesion promoters according to the invention are distinguished, in particular, by a lower volatility and by an increased stability to high temperatures, better stability to boiling water and good dielectric properties of the products prepared therewith. Moreover, the adhesion promoters according to the invention are readily soluble in organic solvents, have low sensitivity to hydrolysis and are stable on storage.

The invention is described in more detail and illustrated in the following examples.

PREPARATION OF STARTING MATERIALS

EXAMPLE A

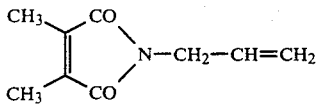

A solution of 57 g (1 mol) of allylamine in 200 ml of toluene is added dropwise to a mixture of 126 g (1 mol) of 2,3-dimethylmaleic anhydride and 500 ml of toluene, with stirring. After the exothermic reaction has subsided, the mixture is refluxed under a water separator until the calculated amount of water has been separated off. The reaction solution is dried over magnesium sulfate and filtered and the filtrate is freed from the solvent in vacuo. The residual oil is distilled under a high vacuum. Boiling point 125°–130° C./2666.6 Pa; yield 154.2 g=93.5% of theory.

This product is employed in Example 21 (as described below).

EXAMPLE B 126 g (1 mol) of 2,3-dimethylmaleic anhydride and 61 g (1 mol) of ethanolamine are reacted by heating at 180° C. for 1 hour to give 150 g of N-(2-hydroxyethyl)-2,3-dimethylmaleimide (boiling point 110° C. under 13.33 Pa; yield 89% of theory). After drying, the N-(2-hydroxyethyl)-2,3-dimethylmaleimide is mixed with 181.5 g (1.78 mols) of acetic anhydride and 3 drops of concentrated sulfuric acid and the mixture is refluxed for one hour in an oil bath heated to 160° C. The acetic acid formed and the acetic anhydride are then distilled off in vacuo. Fractionation of the residue under a high vacuum yields 179 g of N-(2-acetoxyethyl)-2,3-dimethylmaleimide (boiling point 104° C./6.66 Pa; yield 95% of theory). The N-(2-acetoxyethyl)-2,3-dimethylmaleimide is introduced dropwise, under nitrogen, in the course of 75 minutes into a glass column which is filled with Raschig rings and is heated to 550° C. The pyrolysis products are collected at the lower end of the glass column in a cooled receiver. The yellow oil obtained is taken up in diethyl ether and treated with aqueous sodium bicarbonate solution in order to remove the acetic acid. After drying the organic phase over sodium sulfate, the solvent is removed in vacuo and the product is distilled under a high vacuum. In addition to 39.3 g of unconverted starting material, 84.7 g of (N-vinyl)-2,3-dimethylmaleimide are obtained in the form of a yellowish oil; boiling point 58°–60° C./53.33 Pa; yield: 85% of theory, based on converted starting material.

This product is employed according to Example 24 (as described below).

EXAMPLE C

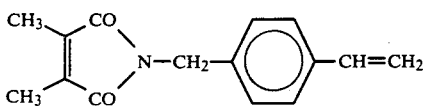

38.1 g (0.25 mol) of 4-chloromethyl-styrene are added slowly dropwise to a suspension of 29.4 g (0.2 mol) of sodium 2,3-dimethylmaleimide [prepared from 2,3-dimethylmaleimide and sodium methylate] in 100 ml of dry N,N-dimethylformamide. After the exothermic reaction has subsided, the reaction mixture is stirred for 1 hour at 60° C. and, after cooling, 500 ml of distilled water are added. The aqueous mixture is extracted with 200 ml of diethyl ether and after drying the organic phase over sodium sulfate the diethyl ether is distilled off. The resulting yellow, viscous oil is freed from solvent residues at 50° C./0.133 Pa. Yield 27.4 g (=57% of theory).

Analysis for $C_{15}H_{15}NO_2$: calculated C 74.67%, H 6.27%, N 5.81%; found: C 74.6%, H 6.5%, N 5.8%.

This product is used as the starting material according to Example 28.

EXAMPLE D

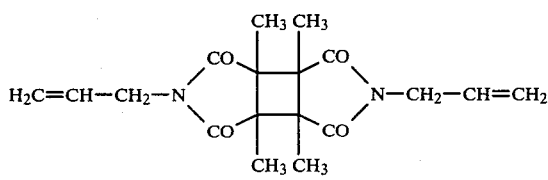

A well-stirred mixture of 20 g (0.121 mol) of (N-allyl)-2,3-dimethylmaleimide [prepared according to Example a)] and 80 ml of dry acetone is irradiated under nitrogen in a water-cooled radiation apparatus (150 watt mercury high-pressure lamp). After 24 hours, the product which has precipitated is filtered off and the filtrate is irradiated for a further 24 hours, after which the product which has precipitated out is again filtered off. The resulting solid product is recrystallised from cyclohexane. After evaporation of the filtrate, the residue is purified by chromatography on silica gel using chloroform as the solvent. Melting point 202° C.; yield 10.1 g=50.5% of theory; molecular weight calculated=330, molecular weight found=337.

This product is used as the starting material in Example 17.

EXAMPLE E

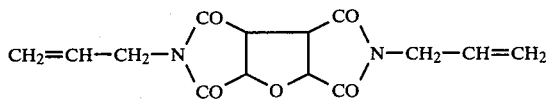

A solution of 57.1 g (1 mol) of allylamine is added dropwise at 20°–40° C. to a mixture of 106 g (0.5 mol) of tetrahydrofuran-tetracarboxylic acid dianhydride and 300 ml of anhydrous N,N-dimethylformamide. After the exothermic reaction has subsided, the reaction mixture is stirred for a further 10 hours at 25° C. A mixture of 500 ml of acetic anhydride and 161 ml of pyridine is then added and the reaction mixture is kept at 30° C. for 3 hours. The clear reaction solution is then evaporated in vacuo and the residue is introduced into 2 liters of distilled water. The resulting fine suspension is filtered and the material on the filter is washed with three times 100 ml of distilled water. The resulting product is dried, first over phosphorus pentoxide and then under a high vacuum. After recrystallisation from toluene, a finely crystalline white powder is obtained. Yield 107 g=84% of theory; melting point 162° C. This product is used as the starting material in Example 18.

PREPARATION OF PRODUCTS OF THE FORMULA I

All of the reactions are carried out in stirred vessels made of glass, which are fitted with a reflux condenser, an internal thermometer, a dropping funnel with a pressure-equalisation device and a stirrer.

The reactions are carried out with the exclusion of atmospheric humidity. All of the reactions with H-Si compounds and the photoreactions are carried out in an atmosphere of dry nitrogen.

The structure and the composition of the products are confirmed by IR, NMR and mass spectroscopy and by elementary analysis.

The molecular weights are determined with the aid of a vapour pressure osmometer.

EXAMPLE 1

(Process A)

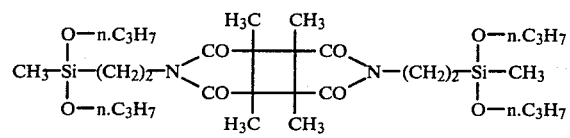

A well-stirred mixture of 20 g (0.063 mol) of 2-(2,3-dimethylmaleimido)-ethyl-di-n-propoxy-methylsilane [prepared according to Example 25] and 90 ml of dry acetone is irradiated under nitrogen in a water-cooled radiation apparatus (150 watt mercury high-pressure lamp) until a thin layer chromatogram (solvent chloroform) of the reaction mixture shows no further starting material. The solution is then evaporated and the residue is recrystallised from 120 ml of n-hexane. After drying under a high vacuum, N,N'-bis-[2-(di-n-propoxy-methyl-silyl)-ethyl]-1,2,3,4-tetramethylcyclobutane-1,2,3,4-tetracarboxylic acid diimide is obtained in the form of a crystalline white powder; melting point 151° C.; yield=11.2 g (56% of theory).

EXAMPLES 2 To 15

(Process A)

The compounds of the formula I

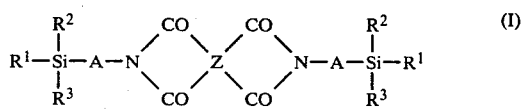

listed in Table I below are prepared by the procedure described in Example 1, thioxanthone in a concentration of 0.5% by weight being added in some cases, as a photosensitiser (+ = addition of thioxanthone).

TABLE I

| Example No. | Z | Thioxanthone | A | $R^1$ | $R^2$ | $R^3$ | Melting point °C. | $M_{calc.}$ $M_{found}$ |
|---|---|---|---|---|---|---|---|---|
| 2 | H3C CH3 / H3C CH3 (cyclobutane) | — | —(CH2)3— | —CH3 | —O—n.C3H7 | —O—n.C3H7 | 61–64 | 655 720 |
| 3 | " | + | " | —OCH3 | —OCH3 | —OCH3 | 127–131 | 574 594 |
| 4 | " | + | " | —OC2H5 | —OC2H5 | —OC2H5 | 103–105 | 658 672 |
| 5 | " | + | —⟨O⟩—O—(CH2)3— | —CH3 | —O—n.C3H7 | —O—n.C3H7 | 208 (decomp.) | 839 881 |
| 6 | " | + | —⟨O⟩—O—(CH2)3— | —CH3 | —O—n.C3H7 | —O—n.C3H7 | 137–139 | 839 855 |
| 7 | " | + | phthalimido-(CH2)3— | —CH3 | —O—n.C3H7 | —O—n.C3H7 | 148–150 | 945 1010 |
| 8 | " | + | —(CH2)3—NH—(CH2)2— | —OCH3 | —OCH3 | —OCH3 | 68–72 | 660 637 |
| 9 | " | — | —(CH2)2—O—(CH2)2— | —CH3 | —O—⟨H⟩ | —O—⟨H⟩ | 76–80 | 874 821 |
| 10 | " | — | —CH2—⟨O⟩—(CH2)2— | —CH3 | —O—n.C3H7 | —O—n.C3H7 | oil | 806 792 |
| 11 | (CH2)4 □ (CH2)4 | + | —(CH2)2— | —CH3 | —O—n.C3H7 | —O—n.C3H7 | oil | 679 672 |

TABLE I-continued

| Example No. | Z | Thioxanthone | A | R¹ | R² | R³ | Melting point °C. | $M_{calc.}$ $M_{found}$ |
|---|---|---|---|---|---|---|---|---|
| 12 | Cl, Cl, Cl, Cl (cyclobutane) | + | —(CH₂)₃— | —CH₃ | —O—n.C₃H₇ | —O—n.C₃H₇ | " | |
| 13 | H, CH₃, CH₃, H (cyclobutane) | + | —(CH₂)₃— | —CH₃ | —O—n.C₃H₇ | —O—n.C₃H₇ | " | 625 / 655 |
| 14 | C₆H₅, H, H, C₆H₅ (cyclobutane) | + | —(CH₂)₃— | —CH₃ | —O—n.C₃H₇ | —O—n.C₃H₇ | " | |
| 15 | (phenanthrene/cyclobutane fused structure) | + | —(CH₂)₃— | —CH₃ | —O—n.C₃H₇ | —O—n.C₃H₇ | " | 803 / 769 |

EXAMPLE 16
(Process A)

Analogously to Example 1, a solution of 10 g (0.025 mol) of N-[3-(methyl-dicyclohexyloxy-silyl)propyl]-2,3-dimethyl-maleimide in 100 ml of acetone is irradiated with UV light for 26 hours. After removing the solvent (finally under a high vacuum at 50° C. and 0.133 Pa), the product is obtained in the form of a clear, colourless, highly viscous oil. The molecular weight is 652; a molecular weight of 815 is calculated for the corresponding dimer $C_{44}H_{74}N_2O_8SI_2$. The product is employed as an adhesion promoter without further purification.

EXAMPLE 17
(Process C)

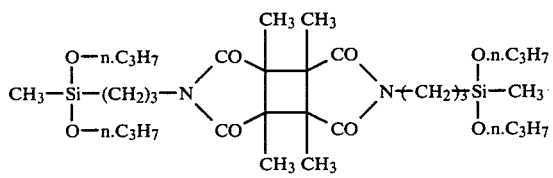

A mixture of 3.1 g (0.094 mol) of the N,N'-bis-(allyl)-1,2,3,4-tetramethyl-cyclobutane-1,2,3,4-tetracarboxylic acid diimide prepared according to Example d and 0.5 ml of a 0.02 molar solution of hexachloroplatinic-(IV) acid in n-propanol and 10 ml of dry xylene is heated to 110° C. under nitrogen. At this temperature, a mixture of 3.0 g (0.188 mol) of methyl-di-n-propoxysilane, 0.5 ml of 0.02 molar catalyst solution and 5 ml of xylene is added slowly dropwise at such a rate that the reaction temperature is 110°–120° C. The reaction mixture is then heated at 120° C. for a further one hour and the solvent is removed in vacuo. After recrystallisation from petroleum ether, the product is obtained in the form of a finely crystalline, white powder; melting point 62°–64° C. Yield 3.9 g=64% of theory.

EXAMPLE 18
(Process C)

Analogously to Example 17, 7 g (0.024 mol) of N,N'-bis-(allyl)-tetrahydrofuran-2,3,4,5-tetracarboxylic acid diimide, prepared according to Example e), 20.2 g (0.048 mol) of tris-n-octyloxy-silane and 1 ml of 0.02 molar $H_2PtCl_6$ solution in 70 ml of dry xylene as the solvent are reacted at 100°–130° C. After the reaction has ended, the catalyst is removed by stirring for one hour with 1 g of active charcoal and then filtering. The clear, pale yellow solution is freed from the solvent in vacuo, finally at 50° C. and under 0.133 Pa. The product is obtained in the form of a clear, yellowish oil. Yield 25 g=92% of theory.

Analysis for $C_{62}H_{118}N_2O_{11}Si_2$: calculated: C 66.2%, H 10.58%, Si 5.00%, N 2.49%; found: C 66.0%, H 10.7%, Si 5.0%; N 2.6%.

EXAMPLE 19
(Process D)

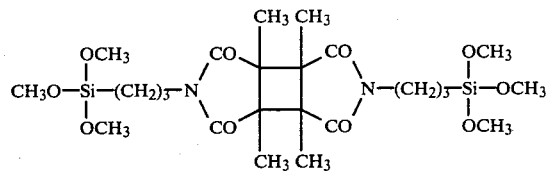

9.5 g (0.048 mol) of 3-chloro-n-propyl-trimethoxysilane are added slowly to a suspension of 5.9 g (0.02 mol) of N,N'-bis-(sodium)-1,2,3,4-tetramethyl-cyclobutane-1,2,3,4-tetracarboxylic acid diimide [prepared from 1,2,3,4-tetramethyl-cyclobutane-1,2,3,4-tetracarboxylic acid diimide and sodium methylate in N,N-dimethylacetamide] in 100 ml of dry dimethylformamide and the mixture is heated at 100° C. for 2 hours. After cooling, undissolved salt is filtered off and the solvent and the excess 3-chloro-n-propyl-trimethoxysilane are distilled off under a high vacuum under 0.133 Pa. The crystalline, white product is purified by recrystallisation from n-hexane. Melting point 129°-131° C.; yield 7.4 g=66% of theory. $M_{calc.}$ 574, $M_{found}$ 586.

PREPARATION OF PRODUCTS OF THE FORMULA XIX

EXAMPLE 20

(Process B')

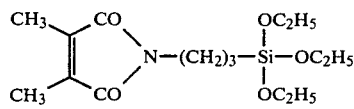

A mixture of 21.8 g (0.173 mol) of 2,3-dimethylmaleic anhydride, 38.3 g (0.173 mol) of 3-aminopropyltriethoxysilane, 500 ml of n-hexane and 0.5 g of pyridine is refluxed under a water separator until the calculated amount of water has distilled over. The reaction mixture is then cooled and the supernatant hexane solution is decanted off from the higher molecular weight products, which have precipitated out. After removing the solvent, 3-(2,3-dimethylmaleimido)-propyl-triethoxysilane is distilled under a high vacuum; boiling point 122° C. (0.133 Pa); yield 30 g=54% of theory.

EXAMPLE 21

(Process C')

24.8 g (0.15 mol) of N-allyl-2,3-dimethylmaleimide and 0.5 ml of a 0.02 molar solution of hexachloroplatinic acid in diethylene glycol dimethyl ether are heated to 120° C. under nitrogen. At this temperature, a mixture of 39.9 g (0.165 mol) of dicyclohexyloxymethylsilane and 0.5 ml of a 0.02 molar solution of $H_2PtCl_6$ in diethylene glycol dimethyl ether are slowly added dropwise at such a rate that the reaction temperature remains within the range of 120°-130° C. After the dropwise addition is complete, a further 0.5 ml of catalyst solution is added and the reaction mixture is heated at 140° C. for one hour. The product [3-(2,3-dimethylmaleimido)-propyl-dicyclohexyloxy-methylsilane] is then distilled under a high vacuum; boiling point 154°-160° C. (0.133 Pa); yield 39.2 g=64% of theory.

EXAMPLE 22

(Process D')

A mixture of 16.3 mol) of potassium 2,3-dimethylmaleimide (prepared by reacting 2,3-dimethylmaleimide with potassium methylate in methanol) and 150 ml of dry N,N-dimethylformamide is heated to 70° C. At this temperature, 19.8 g (0.1 mol) of 3-chloropropyl-trimethoxysilane are added dropwise. After the exothermic reaction has subsided, the reaction mixture is kept at 70° C. for a further 2 hours, and after cooling to room temperature (20°-25° C.) the salt which has precipitated is filtered off. The N,N-dimethylformamide is distilled off under a high vacuum, under 13.333 Pa. The residue is taken up in a little dry diethyl ether, filtered again and, after removing the solvent, fractionated under a high vacuum. 16 g (56% of theory) of 3-(2,3-dimethylmaleimido)-propyl-trimethoxysilane are obtained; boiling point 112° C. (0.133 Pa).

EXAMPLES 23-33

Further compounds of the formula XIX were prepared according to processes B' and C'. The starting materials are listed in Table II and the particular process used is quoted. Examples 20 to 22 have also been included in the Table.

Products of the formula XIX which contain

as Y and also products of the formula XIX which contain

as Y are obtained according to Examples 23 to 29. The products are characterised in Table III with the aid of their molecule groups for formula XIX. Additional Examples 30-33 are also listed in this table.

TABLE II

| Example No. | Silane of the formula $H-Si(R^2)(R^1)(R^3)$ or Silane of the formula V or Silane of the formula X | Monofunctional compound analogous to formula VII or Monofunctional compound analogous to formula IV or Monofunctional alkali metal compound analogous to formula IX | Process of preparation |
|---|---|---|---|
| 20 | 3-aminopropyl-triethoxysilane | 2,3-dimethyl-maleic anhydride | B' |
| 21 | dicyclohexyloxy-methylsilane | N—allyl-2,3-dimethyl-maleimide* | C' |
| 22 | 3-chloropropyl-trimethoxysilane | potassium 2,3-dimethyl-maleimide | D' |
| 23 | 3-aminopropyl-trimethoxysilane | 2,3-dimethyl-maleic anydride | B' |
| 24 | tri-n-propoxysilane | (N—vinyl)-2,3- | C' |

TABLE II-continued

| Example No. | Silane of the formula $H-\underset{\underset{R^3}{\overset{\overset{R^2}{\mid}}{Si}}}{\mid}-R^1$ or Silane of the formula V or Silane of the formula X | Monofunctional compound analogous to formula VII or Monofunctional compound analogous to formula IV or Monofunctional alkali metal compound analogous to formula IX | Process of preparation |
|---|---|---|---|
| 25 | di-n-propoxy-methylsilane | dimethyl-maleimide** (N—vinyl)-2,3-dimethyl-maleimide** | C' |
| 26 | dicyclohexyloxy-methylsilane | $\underset{CH_3}{\overset{CH_3}{\diagdown}}C=C\underset{CO}{\overset{CO}{\diagup}}N-(CH_2)_2-O-CH=CH_2$ | C' |
| 27 | $H_2N-(CH_2)_2-NH-(CH_2)_3-\underset{\underset{OCH_3}{\mid}}{\overset{\overset{OCH_3}{\mid}}{Si}}-OCH_3$ | 2,3-dimethyl-maleic anhydride | B' |
| 28 | di-n-propoxy-methylsilane | $\underset{CH_3}{\overset{CH_3}{\diagdown}}C=C\underset{CO}{\overset{CO}{\diagup}}N-CH_2-\langle O \rangle-CH=CH_2$ (preparation according to Example c) | C' |
| 29 | di-n-propoxy-methylsilane | $\underset{CO}{\overset{CO}{\diagdown}}N-CH=CH_2$*** | C' |

*(Preparation according to Example a)
**(Preparation according to Example b)
***(disclosed in the publication by R. H. Yocum and E. B. Nyquist "Functional Monomers", volume 2, page 234; New York: Dekker (1974))

TABLE III

| Example No. | Process of preparation | $R^{12}$ | $R^{13}$ | $R^8$ | $A_1$ | $R^1$ | $R^2$ | $R^3$ | Boiling point C.° (Pascal) |
|---|---|---|---|---|---|---|---|---|---|
| 23 | B' | —CH₃ | —CH₃ | | —(CH₂)₃— | —OCH₃ | —OCH₃ | —OCH₃ | 117 (1.333) |
| 24 | C' | —CH₃ | —CH₃ | | —(CH₂)₂— | —O—n.C₃H₇ | —O—n.C₃H₇ | —O—n.C₃H₇ | 105 (0.133) |
| 25 | C' | —CH₃ | —CH₃ | | —(CH₂)₂— | —CH₃ | —O—n.C₃H₇ | —O—n.C₃H₇ | 113 (6.666) |
| 26 | C' | —CH₃ | —CH₃ | | —(CH₂)₂—O—(CH₂)₂— | —CH₃ | —O—⟨H⟩ | —O—⟨H⟩ | 175 (1.333) |
| 27 | B' | —CH₃ | —CH₃ | | —(CH₂)₂—NH—(CH₂)₃— | —OCH₃ | —OCH₃ | —OCH₃ | 154 (0.133) |
| 28 | C' | —CH₃ | —CH₃ | | —CH₂—⟨O⟩—CH₂CH₂— | —CH₃ | —O—n.C₃H₇ | —O—n.C₃H₇ | 163–171 (1.333) |
| 29 | C' | | | —(CH₂)₄— | —(CH₂)₂— | —CH₃ | —O—n.C₃H₇ | —O—n.C₃H₇ | 141–150 (0.133) |
| 30 | C' | —Cl | —Cl | | —(CH₂)₃— | —CH₃ | —O—n.C₃H₇ | —O—n.C₃H₇ | 128–135 (0.133) |
| 31 | C' | H | —CH₃ | | —(CH₂)₃— | —CH₃ | —O—n.C₃H₇ | —O—n.C₃H₇ | 118–122 (1.33) |
| 32 | C' | H | —⟨O⟩ | | —(CH₂)₃— | —CH₃ | —O—n.C₃h₇ | —O—n.C₃H₇ | |

TABLE III-continued

| Example No. | Process of preparation | $R^{12}$ | $R^{13}$ | $R^8$ | $A_1$ | $R^1$ | $R^2$ | $R^3$ | Boiling point C.° (Pascal) |
|---|---|---|---|---|---|---|---|---|---|
| 33 | C' | | | | —(CH$_2$)$_3$— | —CH$_3$ | —O—n.C$_3$H$_7$ | —O—n.C$_3$H$_7$ | (decomp.) |

EXAMPLE 34
(Process C')

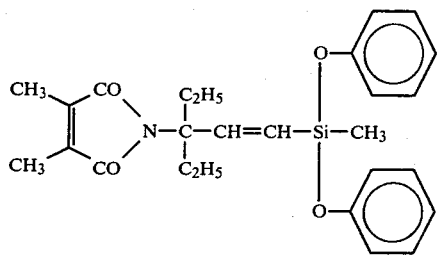

Analogously to Example 21, a solution of 8.4 g (0.038 mol) of N-[1,1-diethyl-propargyl]-2,3-dimethylmaleimide [prepared by reacting 2,3-dimethylmaleic anhydride with 1,1-diethyl-propargylamine; boiling point 136°–140° C./2666.6 Pa] in 10 ml of dry xylene is reacted with a solution of 8.8 g (0.038 mol) of methyldiphenoxysilane in 5 ml of dry xylene, the reaction being catalysed by 0.5 ml of a 0.2% solution of hexachloroplatinic IV acid in n-octanol. After heating at 120° C. for one hour, the reaction mixture no longer displays the characteristic band of the H-Si grouping at 2,200 cm$^{-1}$ in the IR spectrum. After removing the platinum catalyst by stirring for 2 hours with 1 g of active charcoal and then filtering, the solvent is removed in vacuo, finally at 50° C. and under 0.133 Pa. The product is obtained in the form of a yellowish, viscous oil and is employed as an adhesion promoter without further purification. Yield 15.9 g=92% of theory.

Elementary analysis for $C_{26}H_{31}NO_4Si$: calculated: C 69.46%, H 6.95%, N 3.11%, Si 6.25%; found: C 69.2%, H 7.3%, N 3.1%, Si 6.5%.

EXAMPLE 35
(Process C')

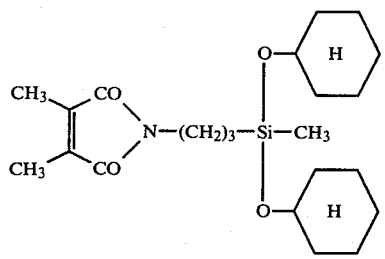

Analogously to Example 34, 184 g (1.11 mols) of N-allyl-2,3-dimethylmaleimide and 138 g (1.12 mols) of methyldichlorosilane, in 1,000 ml of dry xylene as the solvent, are reacted at 100°–115° C., the reaction being catalysed by 2 ml of a 0.02 molar solution of H$_2$PtCl$_6$ in diethylene glycol dimethyl ether. The product is distilled under a high vacuum; boiling point 98°–101° C./0.133 Pa. Yield 168 g=54% of theory.

Elementary analysis for $C_{10}H_{15}Cl_2NO_2Si$: calculated: C 42.86%, H 5.40%, Cl 25.3%, N 5.0%, Si 10.02%; found: C 42.4%, H 5.5%, Cl 25.0%, N 5.1%, Si 10.2%.

16.8 g (0.06 mol) of N-[3-(methyl-dichlorosilyl) n-propyl]-2,3-dimethyl-maleimide are dissolved in 200 ml of dry diethyl ether. A solution of 12 g (0.12 mol) of cyclohexanol and 13.15 g (0.13 mol) of triethylamine in 100 ml of diethyl ether is added slowly dropwise at 20°–35° C. After the addition is complete, the reaction mixture is refluxed for 1 hour and cooled, the triethylamine hydrochloride which has precipitated is filtered off and the filtrate is freed from the solvent in vacuo. The residual colourless oil is distilled under a high vacuum; boiling point 157°–159° C./0.133 Pa. Yield 19.5 g=80% of theory.

EXAMPLE 于
(Process B)

A solution of 9.98 g (=0.0455 mol) of 3-aminopropyl-dipropoxy-methylsilane in 100 ml of N,N-dimethylformamide is added slowly dropwise to a solution of 5.99 g=0.023 mol of 1,2,3,4-tetramethyl-cyclobutane 1,2,3,4-tetracarboxylic acid dianhydride in 650 ml of dry N,N-dimethylformamide, at room temperature, with stirring. The resulting 2% solution of the bis-(amidocarboxylic acid) (I) is stirred for a further 2 hours at room temperature and can be used in the customary manner for impregnating glass fabric. The bisimide (II) is formed when the glass fabric impregnated in this way is subjected to a heat treatment.

Use Example (a) Impregnation of glass fabric

Glass fabric, socalled E-glass, which has a weight of 280 g/m$^2$ and satin weave and has previously been desized by the action of heat to a residual size content of about 0.1% by weight, is impregnated with 2% solutions of the adhesion promoters obtained according to Preparation Examples 24, 1, 6, 7, 16, 17 and 36 and of known adhesion promoters. The adhesion promoter solutions are applied by the dipping process at an impregnation speed of 0.5 m/minute and are then dried for 20 minutes at 180° C. in a circulating air oven.

Prepregs are obtained which have an adhesion promoter content of about 0.09 to 0.12% by weight, based on the glass.

The adhesion promoters (finishes) used are:
(1) No adhesion promoter
(2) Vinyl-tris-(2-methoxyethoxy)-silane ("Silan A 172" from Union Carbide); 2% solution in N,N-dimethylformamide (DMF)

(3) γ-Aminopropyl-triethoxysilane ("Silan A 1100" from Union Carbide); 2% solution in DMF
(4) Chromium chloride-methacrylate complex ("Volan-A" from DuPont); 2% solution in DMF
(5) The product according to Example 1 of U.S. Pat. No. 3,755,354 (γ-maleimidopropyltriethoxysilane); 2% solution in DMF
(6) The diimide according to Example 4 of U.S. Pat. No. 3,901,913; 2% solution in DMF
(7) The diimide according to Example 2a of German Offenlegungsschrift No. 2,504,791; 2% solution in DMF
(I) Adhesion promoter according to Preparation Example 24; 2% solution in DMF
(II) Adhesion promoter according to Preparation Example 1; 2% solution in DMF
(III) Adhesion promoter according to Preparation Example 6; 2% solution in DMF
(IV) Adhesion promoter according to Preparation Example 7; 2% solution in DMF
(V) Adhesion promoter according to Preparation Example 16; 2% solution in DMF
(VI) Adhesion promoter according to Preparation Example 17; 2% solution in DMF
(VII) Adhesion promoter according to Preparation Example 36; 2% solution of the amidocarboxylic acid in DMF.

(b) Production of copper-coated laminate sheets:

1.0 mol of N,N'-4,4'-diphenylmethane-bis-maleimide is dissolved at 100° C. in 500 g of furfuryl alcohol and the solution is cooled to 25° C. 0.4 mol of 4,4'-diaminodiphenylmethane are dissolved at 25° C. in 200 g of 2-methoxyethanol (methylene glycol monomethyl ether). The two solutions are combined and mixed well. Using this solution, the glass fabric finished in accordance with section (a) is impregnated at 25° C. by the dipping process and then dried in a circulating air oven for 18 minutes at 180° C. (resin content of the resulting prepregs 39% by weight). 10 layers of the impregnated fabric are then pressed hot between two 35 microns thick copper foils, which have been pre-treated by electrolytic surfacecoating with brass. The press is initially kept under a light contact pressure for 2–3 minutes and the pressure is then increased to $392.28 \times 10^4$ Pa and the material is pressed for one hour at 180° C. The test pieces are then removed from the press and post-cured for a further 6 hours in an oven at 240° C. (resin content of the resulting laminate sheets 35% by weight).

Properties of the copper-coated laminate sheets thus obtained.

Flexural strength in N/mm² according to ISO/R 178; (a) initial value; (b) after aging for 10 days at 270° C.

Absorption of water in % by weight after 24 hours at 23° C. The measurements are carried out on flexural test pieces according to VSM Standard 77,103.

Dielectric loss factor tgδ/50 Hz according to DIN 53,483; (a) initial value measured at 23° C.; (b) after storing for 6 hours in boiling water.

Dielectric constant $\epsilon_r$/50 Hz according to DIN 53,483; (a) initial value measured at 23° C.; (b) after storing in boiling water for 6 hours.

ISO/R = International Standards Oranisation/Recommendation; VSM = Verein Schweizerischer Maschinenindustrieller; DIN = Deutsche Industrie Norm.

The results are given in Table IV below. Numbering of the test products and of the test pieces is the same as under (a).

TABLE IV

| | Test product No. | | | | | | | | | | | | | |
|---|---|---|---|---|---|---|---|---|---|---|---|---|---|---|
| | 1 | 2 | 3 | 4 | 5 | 6 | 7 | I | II | III | IV | V | VI | VII |
| Flexural strength N/mm² | | | | | | | | | | | | | | |
| (a) Initial value | 422.3 | 401.0 | 586.7 | 553.2 | 427.2 | 465.0 | 429.1 | 402.0 | 401.1 | 508.0 | 461.9 | 430.9 | 453.6 | 501.2 |
| (b) After aging for 10 days at 270° C. | 282.4 | 108.8 | 162.8 | 220.3 | 427.2 | 239.4 | 353.8 | 349.9 | 306.1 | 322.7 | 287.4 | 264.5 | 318.4 | 363.7 |
| Absorption of water in % by weight after 24 hours at 23° C. | 0.53 | 0.28 | 0.29 | 0.23 | 0.24 | 0.26 | 0.25 | 0.27 | 0.19 | 0.13 | 0.13 | 0.19 | 0.13 | 0.22 |
| Dielectric loss factor tgδ/50 Hz | | | | | | | | | | | | | | |
| (a) Initial value | 1.08 | 1.15 | 2.71 | 0.86 | 0.26 | 0.26 | 0.28 | 0.33 | 0.35 | 0.28 | 0.28 | 0.34 | 0.35 | 0.26 |
| (b) After storing in boiling water for 6 hours | 6.57 | 2.81 | 4.22 | 1.93 | 0.65 | 0.55 | 0.45 | 0.73 | 0.78 | 0.55 | 0.65 | 0.61 | 0.61 | 0.57 |
| Dielectric constant $t_r$/50 Hz | | | | | | | | | | | | | | |
| (a) Initial value | 5.1 | 5.4 | 5.1 | 6.6 | 5.0 | 4.7 | 5.1 | 5.3 | 5.3 | 5.2 | 5.3 | 5.4 | 5.5 | 5.0 |
| (b) After storing in boiling water for 6 hours | 6.9 | 5.8 | 5.5 | 7.9 | 5.2 | 4.9 | 5.3 | 5.6 | 5.6 | 5.3 | 5.5 | 5.6 | 5.7 | 5.3 |

What is claimed is:

1. A composition of matter obtained by irradiating a compound of the formula III

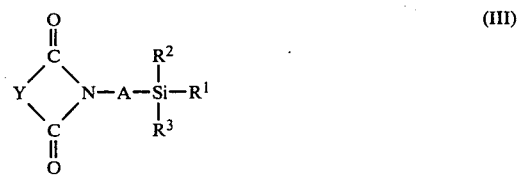

or a mixture of different compounds of the formula III, in which $R^1$ and $R^2$ independently of one another are methyl, ethyl, phenyl, vinyl, chlorine or a group —OR, $R^3$ is chlorine or —OR, R is alkyl having 1–10 C atoms, cycloalkyl having 5–8 C atoms or phenyl, A is a substituted or unsubstituted, divalent, saturated or unsaturated, aliphatic, cycloaliphatic, aliphatic-aromatic or aromatic radical, where the aliphatic radicals A or aliphatic moieties of aliphatic-aromatic radicals A can be interrupted by hetero-atoms, or A is a grouping

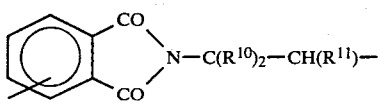

or a grouping

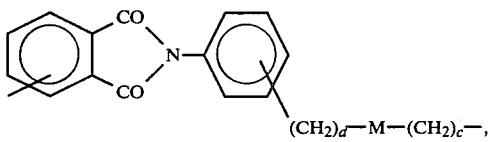

and in the two last-mentioned groupings the bond to the particular N atom is effected via the free valency in the benzene nuclei, $R^{10}$ is hydrogen, methyl or ethyl, $R^{11}$ is hydrogen or alkyl having 1 to 10 C atoms, d is a number from 0 to 6, c is a number from 1 to 6 and M is —O—, —NH— or —N($R^{11}$)—, and in which Y is

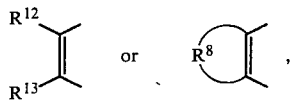

$R^{12}$ and $R^{13}$ independently of one another are hydrogen, methyl, phenyl, —CN or halogen and $R^8$ is alkylene having 3 or 4 C atoms, which can be branched and can be interrupted by a hetero-atom, or is one of the radicals

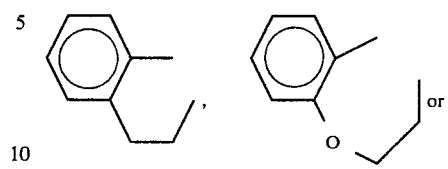

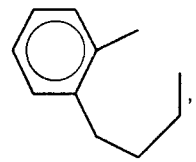

in an organic solvent at temperatures between 5° C. and 120° C. with UV light.

2. A composition according to claim 1 wherein the irradiation with UV light is carried out in the presence of a sensitizer, of benzene or of a mixture of sensitizer and benzene.

3. A composition according to claim 2 wherein the sensitizer is thioxanthone.

4. A composition according to claim 1 wherein $R^1$ is methyl, $R^2$ and $R^3$ are each n-propoxy, A is ethylene and Y is —$CR^{12}$=$CR^{13}$— where $R^{12}$ and $R^{13}$ are each methyl.

5. A composition according to claim 1 wherein $R_1$ is methyl, $R^2$ and $R^3$ are each cyclohexyloxy, A is trimethylene, and Y is —$CR^{12}$=$CR^{13}$— where $R^{12}$ and $R^{13}$ are each methyl.

* * * * *